United States Patent [19]

Jürgens et al.

[11] 4,258,571
[45] Mar. 31, 1981

[54] MAGAZINE WITH CENTERING AND COUPLING ELEMENTS FOR MEASURING AND SAMPLING DEVICES

[75] Inventors: Arnold Jürgens; Herbert Koopmann; Wilhelm Schwarz, all of Wilhelmshaven, Fed. Rep. of Germany

[73] Assignee: Fried. Krupp Gesellschaft mit beschränkter Haftung, Essen, Fed. Rep. of Germany

[21] Appl. No.: 11,376

[22] Filed: Feb. 12, 1979

[30] Foreign Application Priority Data

Feb. 20, 1978 [DE] Fed. Rep. of Germany ....... 2807152

[51] Int. Cl.$^3$ .......................... G01K 1/14; G01N 1/12
[52] U.S. Cl. .......................... 73/425.4 R; 73/DIG. 9; 73/344; 136/234
[58] Field of Search ........ 73/423 R, DIG. 9, 425.4 R; 136/234

[56] References Cited

U.S. PATENT DOCUMENTS

| | | | |
|---|---|---|---|
| 3,559,452 | 2/1971 | Perbix et al. | 73/425.4 R |
| 3,584,511 | 6/1971 | Collins | 73/DIG. 9 |
| 3,638,500 | 2/1972 | Wetzel | 73/DIG. 9 |
| 3,656,347 | 4/1972 | Collins | 73/DIG. 9 |
| 3,717,034 | 2/1973 | Dukelow et al. | 73/DIG. 9 |
| 3,742,763 | 7/1973 | Sczerba | 136/234 |
| 3,916,693 | 11/1975 | Hancart et al. | 73/423 R |
| 4,003,261 | 1/1977 | Nautet et al. | 73/423 R |
| 4,141,249 | 2/1979 | Ishikawa et al. | 73/423 R |
| 4,165,645 | 8/1979 | Cooper | 73/423 R |

FOREIGN PATENT DOCUMENTS 50-36802 11/1975 Japan .................................. 73/DIG. 9

Primary Examiner—Daniel M. Yasich
Attorney, Agent, or Firm—Becker & Becker, Inc.

[57] ABSTRACT

A magazine equipped with centering and coupling elements for measuring and sampling devices for a device for handling the sampling devices by means of measuring lances in melts. The handling device arranged above the vessel adapted to receive and hold the melt is equipped with a lifting mechanism for lifting the measuring lances and is also equipped with a guiding system for guiding a measuring lance. The magazine is displaceable in the direction of its longitudinal axis and is combined with the handling device to form a movable unit with stripping and separating members.

4 Claims, 6 Drawing Figures

MAGAZINE WITH CENTERING AND COUPLING ELEMENTS FOR MEASURING AND SAMPLING DEVICES

The present invention relates to a magazine equipped with centering and coupling elements for measuring and sampling devices. Such magazine is intended for a device for handling the measuring and sampling devices by means of measuring lances in melts. The handling device is arranged above the vessel containing the melt and is provided with a measuring lance lifting mechanism and a measuring lance guiding arrangement. The magazine being displaceable in the direction of its longitudinal axis.

In metallurgical plants and foundries, the property and quality of the melts has to be continuously and carefully supervised and controlled, for instance with regard to temperature and/or the chemical composition. This is done by means of sampling devices which, while utilizing measuring lances, are immersed into the vessel containing the melt, and/or by withdrawing a sample of the melt from the vessel. A magazine of the above mentioned type has become known which cooperates with a stationarily arranged handling device. The device comprising a magazine and the handling device additionally comprises holding pliers and a separating disc arranged in a pivotable arm. The holding pliers and the separating disc are, however, arranged on the handling device which means outside the magazine.

The drawback of this known magazine consists in that the latter when in operative condition has to be moved below the measuring lance and in this way makes the access to the adding and supervising openings difficult or even impossible. The adding and supervising openings are arranged below the guiding means for the measuring lances. A further drawback of the just mentioned known magazine is seen in the fact that the elements for handling the measuring and sample withdrawing devices are only in part arranged on the magazine. The magazine thus does not represent a single unit which without effecting other structural changes could be associated with an already present handling device.

There has furthermore become known a handling device according to which the guiding of the measuring lances is by way of a projecting boom connected to a rotatably mounted standpipe. This movably arranged handling device has associated therewith a locally stationarily arranged magazine which comprises merely centering and coupling members for handling the pertaining measuring sampling devices. The drawbacks inherent to the said stationary arrangement of the known magazine as well as to its design bring about drawbacks particularly consisting in that the measuring lance guiding means have to be displaced with high precision in different pivoting positions, namely in the measuring position, in the coupling disengaging position and in the centering and coupling engaging position. This is disadvantageous with regard to the working operation in view of the normally necessary lifting heights, and is expensive with regard to the necessary control mechanism.

It is, therefore, an object of the present invention to provide in association with a known handling device, a magazine that overcomes the drawbacks of the state of the art as outlined above. More specifically, it is an object of the invention to provide a magazine that is a compact unit which has all elements necessary in connection with the handling of measuring and sampling devices.

It is a further object of this invention to provide a magazine of the above mentioned type which is so designed and in which the magazine is associated with the handling device in such a manner that the surveying and checking of melts by means of a measuring and sampling device will be improved and facilitated while simultaneously the interference with regard to the checking and surveying in connection with the operation concerning the melting process will be reduced.

These and other objects and advantages of the invention will appear more clearly from the following specification in connection with the accompanying drawings, in which:

FIG. 5b is a section taken along the line Vb—Vb of FIG. 5a.

Figure 1:
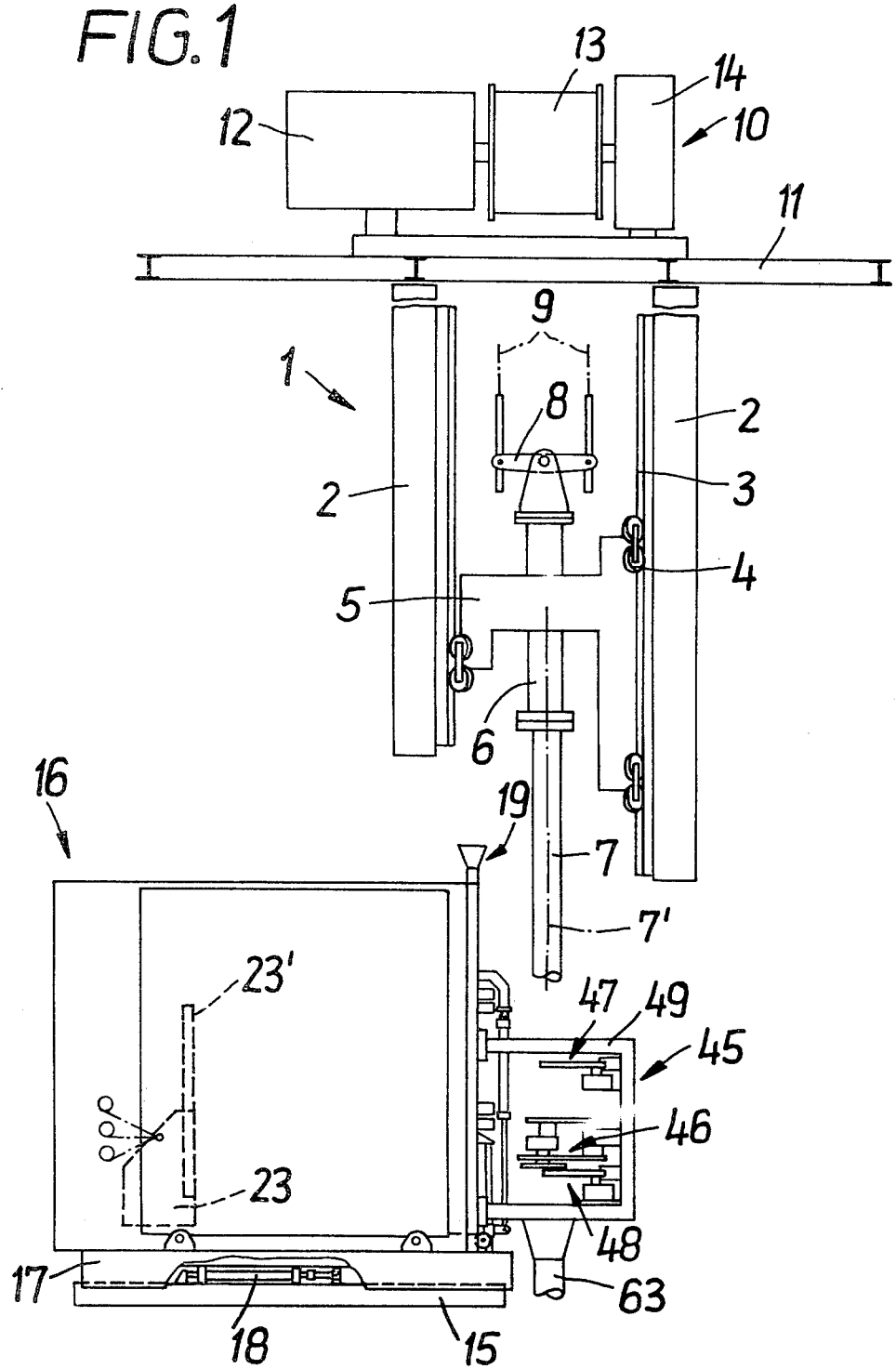
FIG. 1 is a view of a magazine according to the invention with a pertaining handle device.

The present invention is characterized primarily in that the magazine combined with the handling device into a movable unit is equipped with stripping and separating elements.

Referring now to the drawings in detail, the handling device 1 (see FIG. 1) comprises as important components thereof longitudinal beams 2 having associated therewith guiding rails 3. A displaceable carriage 5 equipped with supporting rollers 4 rests on said guiding rails 3. The carriage 5 comprises a connecting member 6 having fastened thereto a measuring lance 7.

The carriage 5 is on one hand connected to a measuring lance lifting mechanism 10 by means of a double cable line 4 pivotally connected to a pivotable lever 8. This double cable line 9 is connected by a platform 11 to the upper end section of the longitudinal beam 2.

The measuring lance lifting mechanism 10 primarily comprises a lifting motor 12, a winch 13 for receiving the double cable line 9, and a braking mechanism 14.

The guiding means for the measuring lances by way of the longitudinal beams 2 (not shown in detail) is connected to a bearing construction 15 on which the magazine 16 through the intermediate arrangement of suitable guiding rollers movably rests by way of a base plate 17 for movement in longitudinal direction. The longitudinal displacing device of the magazine 16 comprises a cylinder piston unit 18 which is arranged above the bearing construction 15 and which is pivotally connected to the bottom plate 17 as well as to the bearing construction 15.

Within the parallelepiped shaped housing of the magazine 16, there are provided three storage devices known per se and extending parallel to each other for receiving the measuring and sampling devices. On that side of the magazine 16 which faces toward the guiding means for the measuring lances with the longitudinal beams 2, the magazine 16 has its central area provided with a centering element 19 which comprises two funnel sections 21 which are pivotable about shafts 20. The size of the passages confined by the funnel sections 21 is adjustable by means of adjusting screws 22 (FIG. 3).

Each of the storage devices has as a movable confining wall, a storage carriage 23 equipped with a vertical supporting plate 23'. The carriage 23 is supported and displaceable in the longitudinal direction of the magazine 16. The storage carriages are connected to a conveyor belt 25 as far as to the region of the front deflecting rollers 24 associated with the storage devices. The measuring and sampling devices provided in the magazine rest upon said conveyor belt 25. The conveyor belt 25 outside the region of the deflecting rollers 24 merges with a cable line 26 which by way of lower deflecting rollers 27 and upper deflecting rollers 28 is guided into the region of the back side of the magazine. A weight 29 is connected to the cable line 26. The measuring and sampling devices provided in the individual storage devices of the magazine 16 thus by way of the pertaining storage carriages 23 and conveyor belt 25 are moved by gravity in the direction of the end face of the magazine 16 thereby coming into the region of the centering member 19. See British Pat. Nos. 1,493,720 published Nov. 30, 1977 and 1,529,745 published Oct. 25, 1978, incorporated herein by reference.

Figure 2:
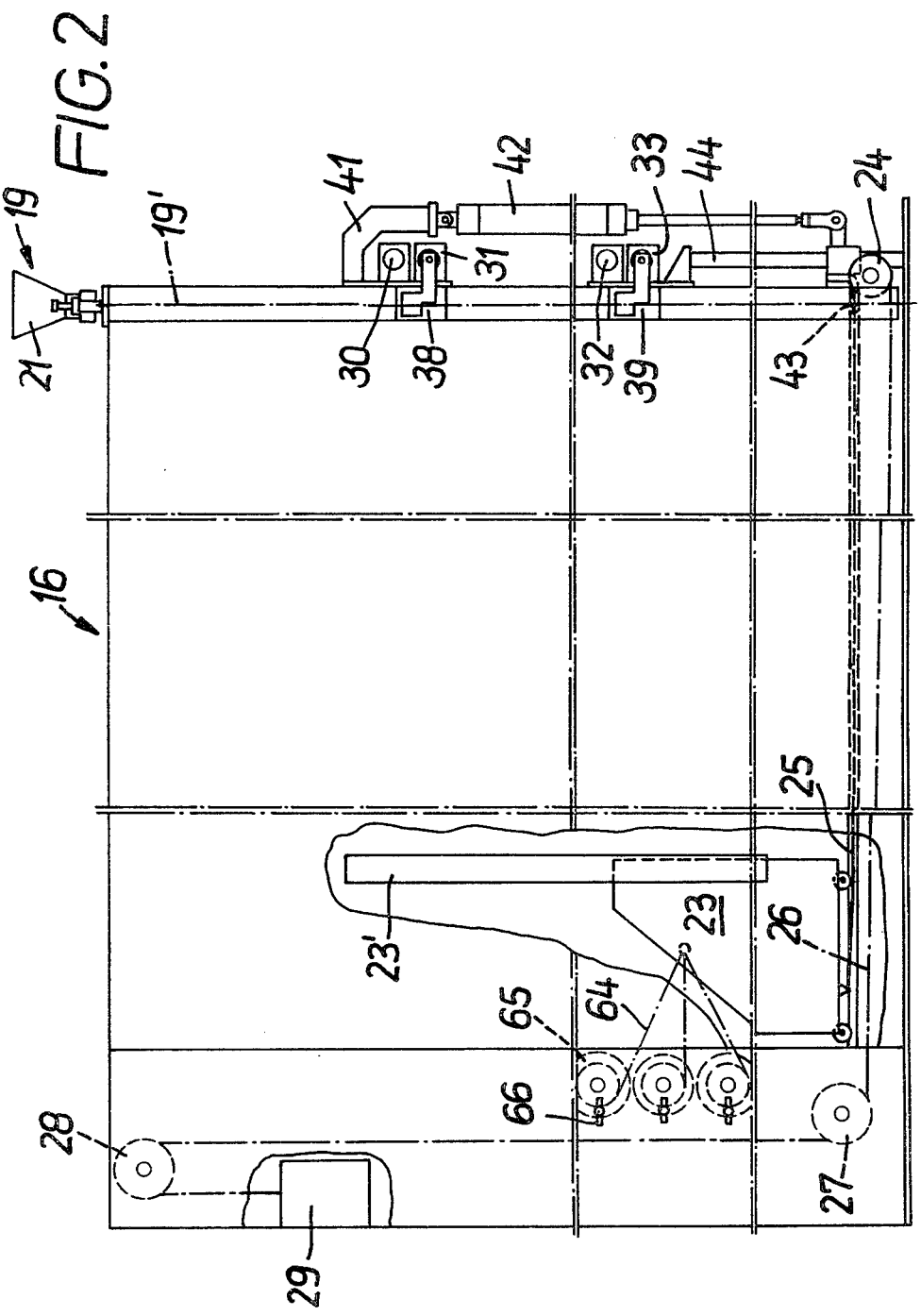
FIG. 2 is a side elevational view of a magazine according to the invention drawn to a larger scale than FIG. 1 but shown with the stripping and separating elements removed.

Each of the three storage carriages 23 by way of a cable line 64 is connected to a manually operable winch 65. The winch 65 is arrestable by arresting bolts 66 (FIG. 2). The winches 65 make it possible to displace the storage carriages 23 against the force exerted by the weights 29, in the direction of the back side of the magazine 16.

Figure 3:
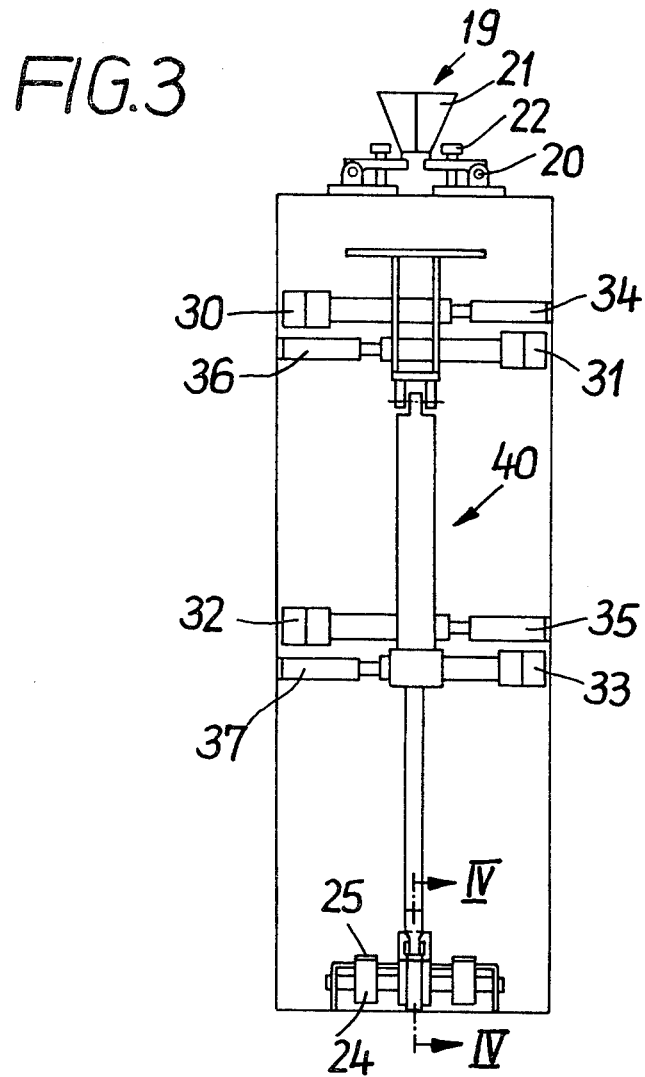
FIG. 3 shows a view of the front side of the magazine facing toward the guiding means for the measuring lances.

The end face of the magazine 16 is provided with a transverse displacing device which comprises two displacing cylinder pairs arranged one above the other and designated with reference numerals 30, 31 and 32, 33 (FIGS. 2,3). These cylinder pairs through displacing members 34, 35 on the right hand side and through displacing members 36, 37 on the left hand side engage lateral recesses 38, 39 in the magazine housing below the centering member 19. The displacing members provided with prism shaped recesses serve for moving one of the front measuring and sampling devices in one of the storage devices into a position below the centering member 19.

Figure 4:
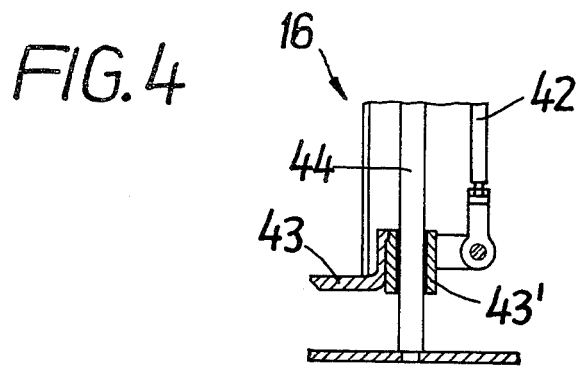
FIG. 4 represents a section taken along the line IV—IV of FIG. 3.

Arranged on the end face of magazine 16 is a coupling member 40 which comprises a supporting arm 41, a cylinder piston unit 42 pivotally connected to said supporting arm 41, and an angle iron 43 which below the conveyor belt 25 (FIG. 2) from the end face of magazine 16 engages the region below by centering member 19 (FIG. 4). The guidance of the angle iron 43 equipped with a sliding bushing 43' is effected by way of a vertically arranged guiding bar 44 which rests upon the top side of the bottom plate of magazine 16. The coupling member 40 serves for lifting the measuring or sampling device arranged on the angle plate 43, in the direction of the centering member 19 thereby coupling said measuring or sampling device to the measuring lance 7 (FIG. 1). The maximum stroke to be carried out by the coupling member 40 preferably amounts to about 400 mm.

The magazine 16 has its end face toward the measuring lance 7 furthermore equipped with a separating station 45 which includes a separating member 46 and stripper member 47,48 and having connection with a frame 49 accordingly being combined into a unit by way of this frame 49 (see FIG. 1).

The frame 49 which is preferably composed of hollow profiles is connected to the end face of the magazine 16 by way of flanges 50 below the centering member 19 (FIG. 1).

Figure 5A:
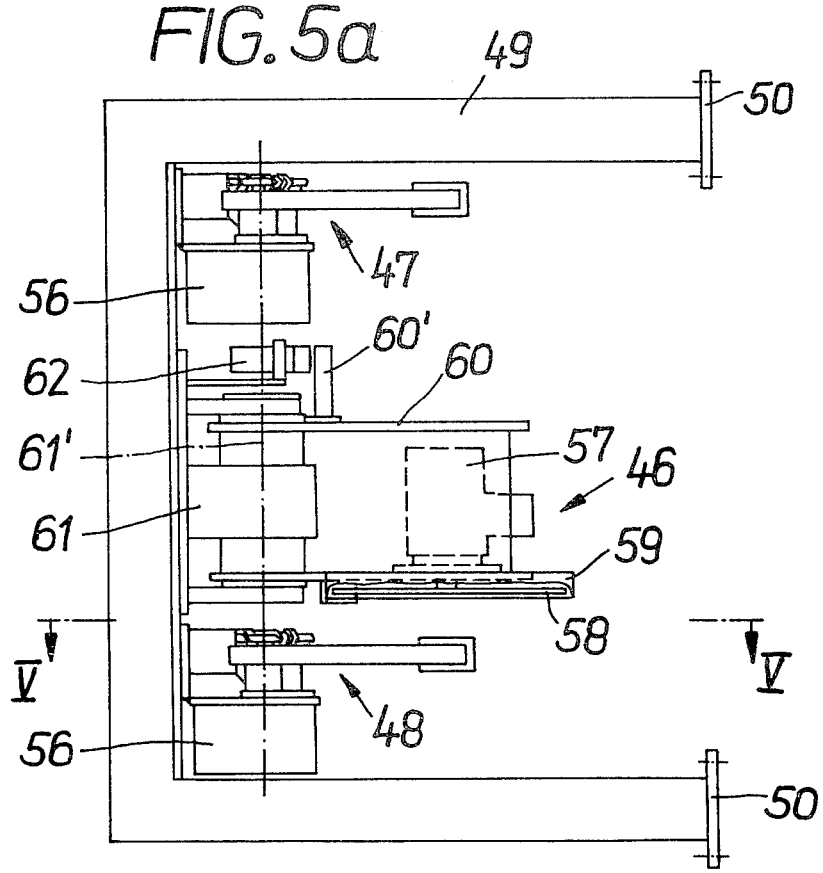
FIG. 5a is a side view of the separating station equipped with the stripping and separating elements.
Figure 5B:
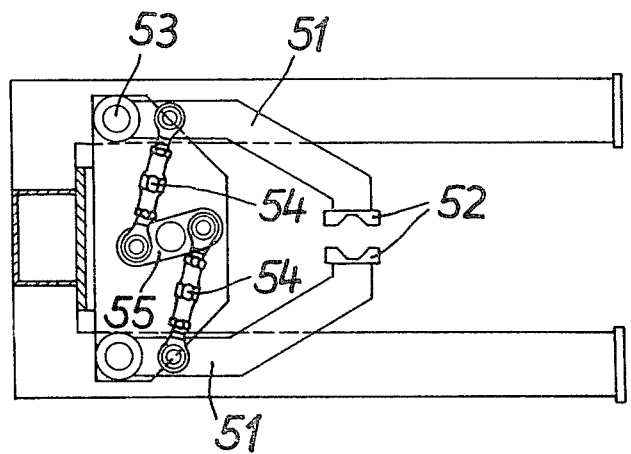

Each stripper member 47, 48 respectively comprises holding arms 51 with clamping jaws 52 which are pivotally arranged about the pivot shafts 53 (FIG. 5b). The adjustment of the holding arms 51 is effected by way of joint levers 54 which through a double lever 55 are connected to a rotary motor or drive 56. The levers 54 are preferably provided with turnbuckles so that the lift brought about by the rotary drive 56 or the clamping force exerted by the latter can be infinitely adjusted without actuating the rotary drive.

The separating member 46 substantially comprises a separating disc 58 moved by means of a rotary drive 57, said separating disc 58 rotating in a protective housing 59 (FIG. 5a).

The rotary drive 57 by way of a pivotal housing 60 is connected to a rotary cylinder 61 which similar to the rotary drives 56 is connected to the vertically arranged end face of frame 49. The adjusting range of the rotary cylinder 61 is adjustable by way of an abutment 60' connected to the pivotal housing 60. The abutment 60' cooperates with an inductive and capacitive proximity switch 62. The operation of the magazine 16 is as follows: for purposes of loading the magazine 16, the storage carriages 23 associated with the individual storage devices by means of the pertaining hand crank 65 are pulled in the direction of the back side of the magazine 16 and after reaching the desired end position are locked in their respective position by introducing the arresting bolts 66. After insertion of the measuring and sampling devices into the magazine, the arresting bolts 66 are relieved and consequently the sampling devices are moves by way of the storage carriages 23 and the pertaining conveying belts 25 by means of the weights 29 in the direction of the centering member 19, i.e. in the direction of the measuring lance guiding means composed of the longitudinal beams 2 while the front measuring and sampling devices engage the prism shaped recesses of the displacing pieces 34–37. The transport of a certain measuring and sampling device below the centering member 19 is brought about by moving either the right hand side or the left hand side displacing pieces 34, 35 and 36,37 respectively toward the outside by means of the pertaining cylinder piston units. The measuring or sampling device held by the displacement pieces after reaching the position below the centering member 19 will have been placed upon the angle irons 43 adjustable as to height.

For purposes of carrying out a measuring or sampling operation, the magazine 16 with the measuring or sampling device is located below the centering member 19 moved in the direction of the measuring lance 7 until the measuring lance axis 7' coincides with the withdrawal axis 19' which latter is determined by the centering member 19. Finally, the measuring lance 7 is moved by the centering member 19 into the magazine 16, and the measuring or sampling device placed in readiness is lifted by means of the coupling member 40 to such an extent that it becomes coupled to the measuring lance 7. Following this coupling operation, the measuring or sampling device by means of the measuring lance 7 is pulled out of the magazine 16 is returned to the position shown in FIG. 1. The separating station 45 is so designed that the measuring lance 7 with the coupled on measuring or sampling device can pass therethrough when the stripping members 47, 48 and the separating member 46 are in their rest position.

For separating the measuring or sampling device, the latter by means of measuring lance 7 is lifted into the region of the separating station 45. As soon as this separating station has been reached, the measuring or sampling device is held fast by pivoting the pair of holding arms 51. The reaching of the closing position is in connection therewith ascertained by the inductive and capacitive proximity switch which is associated with the pairs of holding arms. During the sample withdrawal, the separating disc 58 is moved with respect to the measuring lance 7 by acutation of the rotary cylinder 61 so that the separating disc 58 carries out a pivot movement resulting in the cutting procedure or operation. Following the cutting operation and opening the lower holding arm pair, the separated sample passes onto a transporting device which comprises primarily a withdrawing pipe 63. That end section of pipe 63 which is located at the top is expediently displaceably arranged, whereas the adjacent part is stationary outside the region of the measuring lance axis 7' (FIG. 1).

The remainder of the sampling device or the used up measuring sampling device is thrown into the vessel containing the melt. The advantage obtained by the present invention consists primarily in that the magazine is designed as a compact unit and is movable with regard to the measuring lance guiding means serving as supporting construction in such a way that its handling elements are moved into the required working position. In other words, it is not necessary to move the guiding means for the measuring lances together with the pertaining measuring lance, i.e., also structural elements with considerable dimensions and masses, relative to the magazine into one or more definite positions.

In summary, the handling device provides a convenient apparatus for use in monitoring a metal melt wherein the handling device handles both measuring lances and melt samples. Primarily, the handling device includes a coupling means for connecting member 6 which is positioned above the metal melt (not shown) for holding and hoisting measuring lances 7 and melt samples (which are simply cylindrical rods). The coupling means or connecting member 6 is hoisted by a guiding device consisting of the vertically oriented rails 2. A moveable magazine 16 is provided for storing lances and sampling probes prior to their utilization. The magazine is reciprocated by action of hydraulic cylinder 18 and the measuring lances and sampling probes are mounted on a carriage 23 which itself reciprocates within the magazine 16. Attached to the front of the magazine 16 is a stripping and separating device 45 which includes a pair of axially spaced clamping jaws 47 and 48 that grip individual measuring lances or sampling probes and hold the lances or sampling probes prior to their detachment from the coupling member 6. If a melt sample held by a measuring probe is to be separated or detached, a saw 46 having a cutting blade or cutting disc 58 is rotated by operation of the rotary cylinder 61. In order to lift the measuring lances or probes from the carriage 23 in the magazine 16 an angle iron platform 43 is raised by a hydraulic cylinder 42. A convenient and efficient probe and lance operating device is thereby provided.

What we claim is:

1. In combination, a handling device for use in monitoring a metal melt wherein the handling device handles both measuring lances and melt samples: the handling device comprising:

coupling means positioned above the metal melt for holding and hoisting measuring lances and melt samples;

guiding means for guiding the coupling means;

a moveable magazine for storing measuring lances and sampling probes;

means for moving the magazine toward and away from the coupling and guiding means;

a storage carriage in the magazine for storing measuring lances and sampling probes in a vertical orientation;

means for reciprocating the storage carriage within the magazine in the same direction that the magazine reciprocates whereby the probes and lances are moved in and out of alignment with the coupling and guiding means;

a stripping and separating device secured to the forward end of the magazine for movement with the magazine in and out of alignment with the coupling and guiding means, said stripping and separating means including two clamping jaws axially spaced from one another for gripping individually measuring lances and melt samples upon removing the lances and samples from the melt and hoisting the lances and samples to extend between the jaws for gripping thereby; the stripping and separating means further including a cutting member disposed between the jaws for cuttinhg and thereby separating melt samples from the coupling means.

2. The combination according to claim 1, which includes a transporting device operatively associated with said stripping and separating elements.

3. The combination according to claim 1 further including means inside of the front end of the magazine for lifting the measuring lances or sample probes for engagement by the coupling means.

4. The combination of claim 1 further including a proximity switch of the inductive and capacitive type for limiting rotation of the cutting member.

* * * * *